United States Patent [19]

Karasikov et al.

[11] Patent Number: 5,064,765

[45] Date of Patent: Nov. 12, 1991

[54] ASSAY FOR DETERMINING THE PROPENSITY OF A PERSON TO FORM KIDNEY STONES

[76] Inventors: Nir Karasikov, 3 Biram St., Haifa; Sara Sarig, 19, Hamaapilim St., Jerusalem, both of Israel

[21] Appl. No.: 486,848

[22] Filed: Mar. 1, 1990

[30] Foreign Application Priority Data

Mar. 2, 1989 [IL] Israel .................................. 89447

[51] Int. Cl.$^5$ ...................... G01N 15/02; G01N 21/47
[52] U.S. Cl. ......................................... 436/4; 436/164;
    436/165; 422/73; 422/245; 356/318; 356/335
[58] Field of Search ................... 436/4, 108, 164, 165;
    422/73; 356/318, 335; 422/62, 245, 252, 253

[56] References Cited

U.S. PATENT DOCUMENTS 4,025,307  5/1977  Randolph et al. ............... 23/230 B
4,183,729  1/1980  Randolph ....................... 23/230 B
4,263,010  4/1981  Randlph ........................ 23/230 A Primary Examiner—David L. Lacey
Assistant Examiner—David Redding
Attorney, Agent, or Firm—Oblon, Spivak, McClelland, Maier & Neustadt

[57] ABSTRACT

There is provided an assay for determining the propensity of a person to develop a certain type of kidney stones which is based on the inter-action of the urine of such a person with aqueous solutions of compounds which interact to form such stones. The number and size distribution of resulting particles is determined and the results are evaluated. There is further provided a device for carrying out such an assay, comprising means for interacting the urine of the patient with two solutions containing compounds which form kidney stones, means for breaking up crystal aggregates and means for passing a light beam through the sample positioned in a transparent container, and means for determining the number and size of the resulting particles.

4 Claims, 1 Drawing Sheet

ASSAY FOR DETERMINING THE PROPENSITY OF A PERSON TO FORM KIDNEY STONES

FIELD OF THE INVENTION

The invention relates to a novel method for determining the tendency of a person to develop kidney stones, and especially kidney stones of the oxalate type. The invention further relates to a device for carrying out such measurements and for their evaluation.

Other and further features of the invention will become apparent hereinafter.

BACKGROUND OF THE INVENTION

The formation of stones in a kidney is a common pathological condition in humans. There exist a variety of kidney stones, according to their chemical composition, the most common consisting of calcium oxalate,-calcium phosphate and magnesium ammonium phosphate. It is important to find out whether a person has an inclination to form kidney stones, and of which type. This has been determined up to now mainly after surgery by analysis of the removed stones. In U.S. Pat. No. 4,399,003 there is described a method for diagnosing a patient's proneness to develop calcium oxalate kidney stones, which is based on an assay involving the urine of the patient and calcium and oxalate ions. The measurement is made by means of a calcium ion specific electrode. The present invention relates to an improvement of the said method.

SUMMARY OF THE INVENTION

The invention relates to a method for determining the tendency of a person to develop kidney stones, especially of the oxalate type. The invention further relates to a device for carrying out such an assay. The formation of such kidney stones involves two simultaneous processes: growth of the individual crystals, and their aggregation to form rather large aggregates, resulting in a decrease in the number of individual crystals.

The assay of the invention is carried out with a special attachment to an existing system produced by Messrs. GALAI LTD., which is designed as CIS-1.

The novel attachment comprises a reaction cuvette equipped with a stirrer, with two inlets for ionic solutions, and with a sonification probe. A peristaltic or other suitable type of pump circulates the liquid from the reaction cuvette through the measurements flow cell. There is provided a laser beam, e.g. helium, neon, which is passed through a predetermined volume of the flow cell, the output of this beam being analyzed and evaluated. An algorithm is used to calculate various moments of instantaneous size distribution, and these moments are tracked as a function of time. The urine of the patient, or a sample thereof diluted to a predetermined extent, is introduced into the cuvette, one of the constituents of oxalate stones, for example calcium ions is supplied via one entrance port (generally via a syringe), the other, oxalate ions, via the other entrance port, and this in such a manner as to form a saturated or even supersaturated solution with respect to calcium oxalate.

According to a preferred embodiment concentrated calcium chloride and sodium oxalate solutions are introduced in a controlled manner and quantity into the cuvette which contains a measured quantity of urine, which is previously centrifuged, so as to obtain a final solution of 1 mM, which is allowed to ripen for 15 minutes.

After this period of time the particle size distribution (PSD) is determined by means of the Galai Computerized Inspection System (CIS-1) using a laser beam for scanning the suspension.

The CIS-1 system determines the size distribution of the crystallites, by means of the specific attachment developed for this purpose. There is determined the size of the individual particles by means of a rotating focused laser beam which scans a certain volume of the tested suspension. The rate of rotation is a predetermined constant one: the larger the signal resulting from the interaction of the beam with a particle, the larger is the size of such particle. The concentration of particles per unit volume is also measured, and this by the rate of interaction between beam and particles.

Figures 1, 1A:
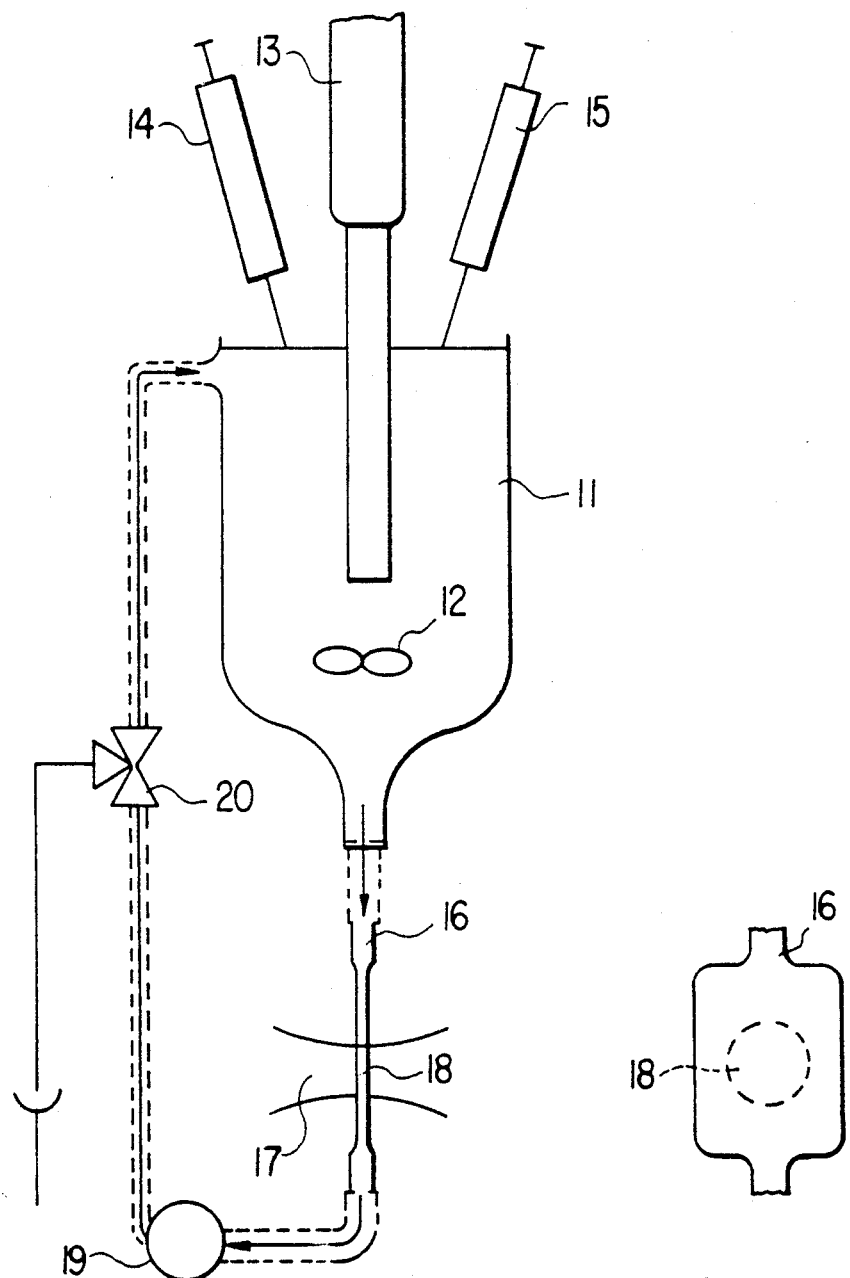
FIG. 1 is a schematic illustration of the device for performing the assay.
FIG. 1a is an enlarged cross-sectional view of the microflow cell 16 of the device.

The specific device is schematically set out in FIG. 1, which is a sectional elevational side-view, not according to scale, in which: 11, is the reaction container, provided with a stirrer, 12, and a sonication probe, 13. There are provided two syringe type devices 14 and 15, which can be operated so as to introduce simultaneously quantities of ionic solutions, such as calcium chloride and sodium oxalate. The flow enters a narrow cross-section of the flow cell 16 (microflow cell), in which a laser beam 17 scans the volume 18 at the narrow part of the cell 16. A pump 19 circulates the suspension from the reaction container 11 to the microflow measurement cell 16, and back again. A threeway valve 20, enables cleaning and washing of the system after measurement.

The solutions from 14 and 15 are introduced into a sample of the urine in container 11 and start a process of crystallization and aggregation of calcium oxalate crystallites. The sonication device 13 is used to break up any aggregates which may be present so that at the start of the measurement no such aggregates are present in the system.

At this stage the measurement commences, and there is determined the dynamics of crystal growth and aggregation of crystals to form clusters (aggregates). The entire process is advantageously computer-controlled so that the assay is carried out in a practically automated manner, with a plotting and evaluation of the results. Sonication (20 W, 3 mm tip, 40 KHz) for a few seconds is adequate to eliminate aggregates. At this stage, measurement of number and size of particles is measured against time. There exists a significant difference between a person having a propensity to develop calcium oxalate stones and one who is not prone to such development. It is very likely that the urine of a healthy person contains a component which hinders aggregate formation. It is clear that when aggregates form, the overall number of individual particles decreases drastically, and thus there is provided a clear criterion for distinguishing between healthy persons and those who have an inlication to stone formation. According to the present invention, it is possible to carry out measurements in undiluted urine; the assay is not restricted to oxalates only as it is possible to introduce aqueous solutions of other stone-formers and to evaluate the inclination to form aggregates of resulting crystals; the simultaneous measurement of both particle number and aggregate size provides a very accurate and reliable method. As blank (control), there can be used a sample of synthetic urine.

An algorithm calculates various moments of instantaneous distribution. These moments are tracked as a function of time.

Thus, in a similar manner the ionic solutions can be such as to form calcium phosphate or any other composition which forms kidney stones. A typical laser used is a HeNe laser having an output of the order of 2 mW, the beam of which is collimated to a diameter of the order of from about 200 $\mu$m to about 1 mm diameter. Advantageously, the laser beam is rotated, and good results were obtained at a rate of the order of 6000 RPM.

The above values are of an indicative nature only.

We claim

1. An assay for determining the propensity of a person to form kidney stones of a certain type which comprises inserting a urine sample into a transparent container, introducing into such container simultaneously aqueous solutions of soluble compounds which interact to form the compound of the kidney stone, sonicating the sample for a length of time sufficient to eliminate aggregates and determining particle size and number of said compound of the kidney stone over a certain period of time.

2. An assay according to claim 1, wherein the inclination to form kidney stones consisting essentially of oxalates is measured and wherein said aqueous solutions comprises calcium and oxalate ions.

3. An assay according to claim 1, wherein a laser beam is passed through the container and said particle size and number is determined.

4. An assay according to claim 3, wherein the laser beam is rotated.

* * * * *